(12) United States Patent
Dalton et al.

(10) Patent No.: US 9,201,041 B2
(45) Date of Patent: Dec. 1, 2015

(54) EXTENDED GATE SENSOR FOR PH SENSING

(71) Applicant: INTERNATIONAL BUSINESS MACHINES CORPORATION, Armonk, NY (US)

(72) Inventors: Timothy J. Dalton, Ridgefield, CT (US); Ashish V. Jagtiani, Tarrytown, NY (US); Ramachandran Muralidhar, Mahopac, NY (US); Sufi Zafar, Briarcliff Manor, NY (US)

(73) Assignee: GLOBALFOUNDRIES INC, Grand Cayman (KY)

( * ) Notice: Subject to any disclaimer, the term of this patent is extended or adjusted under 35 U.S.C. 154(b) by 114 days.

(21) Appl. No.: 13/967,006

(22) Filed: Aug. 14, 2013

(65) Prior Publication Data

US 2014/0370636 A1 Dec. 18, 2014

Related U.S. Application Data

(63) Continuation of application No. 13/918,272, filed on Jun. 14, 2013.

(51) Int. Cl.
*G01N 27/414* (2006.01)
(52) U.S. Cl.
CPC .................................... *G01N 27/414* (2013.01)
(58) Field of Classification Search
CPC .................. G01N 27/414; H01L 2924/13073; H01L 2924/13072
See application file for complete search history.

(56) References Cited

U.S. PATENT DOCUMENTS

| 7,948,015 | B2 | 5/2011 | Rothberg et al. |
| 8,062,488 | B2 | 11/2011 | Chou et al. |
| 2004/0035699 | A1 | 2/2004 | Hsiung et al. |
| 2006/0197118 | A1 | 9/2006 | Migliorato et al. |
| 2011/0159481 | A1 | 6/2011 | Liu et al. |
| 2012/0021918 | A1 | 1/2012 | Bashir et al. |
| 2014/0264470 | A1* | 9/2014 | Fife et al. ...................... 257/253 |

OTHER PUBLICATIONS

Chin, Y., et al. "Titanium Nitride Membrane Application to Extended Gate Field Effect Transistor pH Sensor Using VLSI Technology" Japanese Journal of Applied Physics, vol. 40, No. 11. Jul. 2001. pp. 6311-6315.
Hammond, P., et al. "A System-On-Chip Digital pH Meter for Use in a Wireless Diagnostic Capsule" IEEE Transactions on Biomedical Engineering, vol. 52, No. 4. Apr. 2005. pp. 687-694.
Liao, Y., et al. "Fabrication and Characterization of a Ruthenium Nitride Membrane for Electrochemical pH Sensors" Sensors 2009. Apr. 2009. pp. 2478-2490.

(Continued)

*Primary Examiner* — Evan Pert
*Assistant Examiner* — Leslie Pilar Cruz
(74) *Attorney, Agent, or Firm* — Tutunjian & Bitetto, P.C.

(57) ABSTRACT

A sensing device includes a substrate having a source region and a drain region formed therein. A gate structure is formed over the substrate and includes a gate dielectric and a gate conductor. The gate conductor is formed on the gate dielectric and disposed between the source region and the drain region. A dielectric layer is formed over the substrate and has a depth configured to form a well over the gate conductor. A gate extension is formed in contact with or as part of the gate conductor and including a conductive material covering one or more surfaces of the well.

13 Claims, 5 Drawing Sheets

(56) References Cited

OTHER PUBLICATIONS

Rothberg, J., et al. "An Integrated Semiconductor Device Enabling Non-Optical Genome Sequencing" Nature, vol. 475. Jul. 2011. pp. 348-352.

Sakata, T., et al. "Potential Behavior of Bio-Chemically Modified Gold Electrode for Extended Gate Field Effect Transistor" Japanese Journal of Applied Physics, vol. 44, No. 4B. Apr. 2005. pp. 2860-2863.
m \* cited by examiner

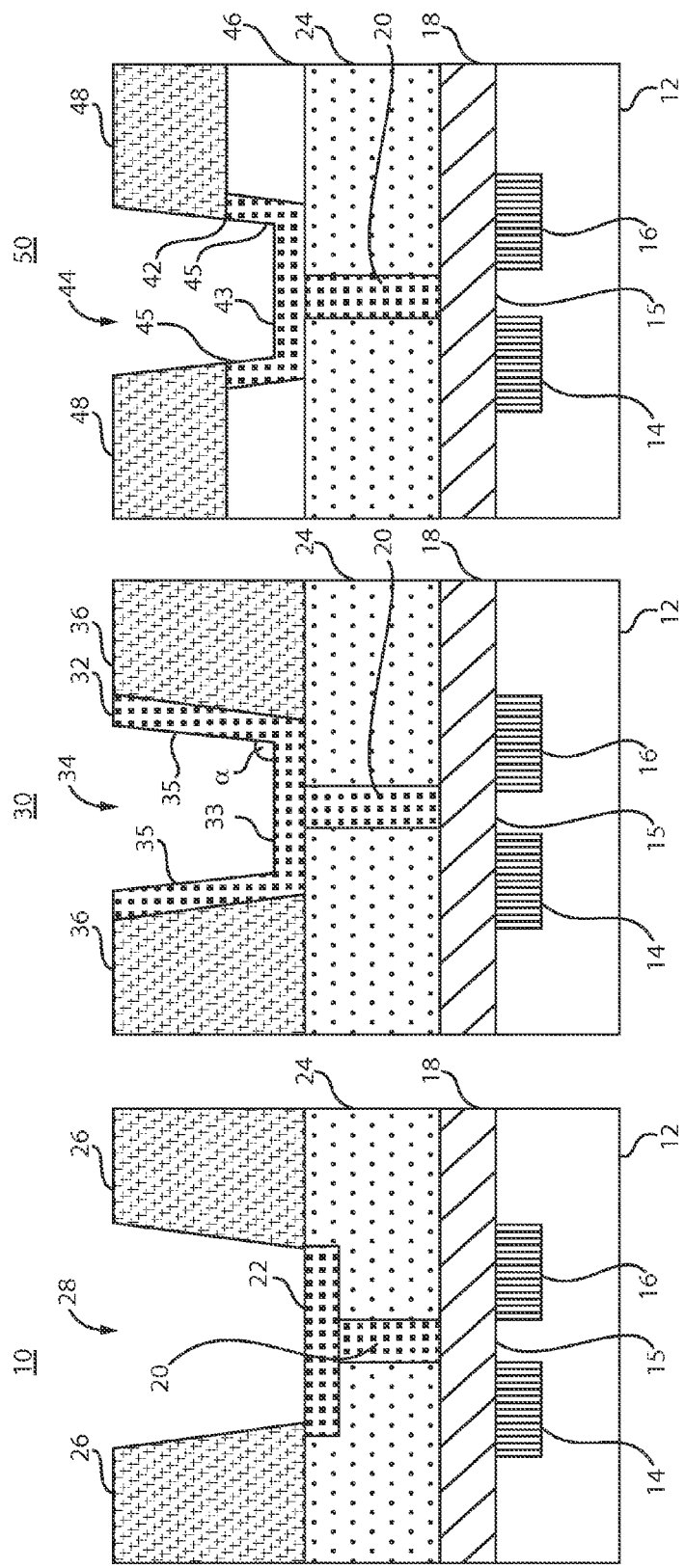

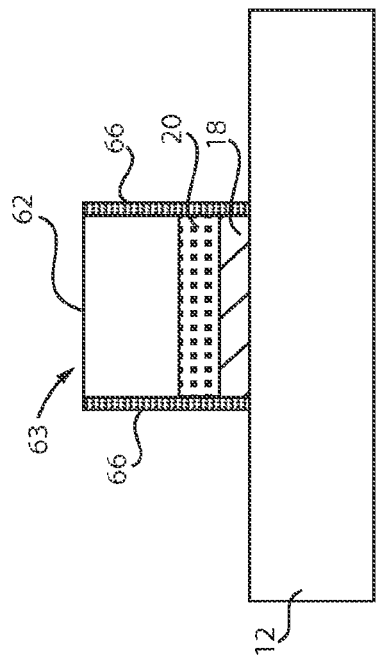
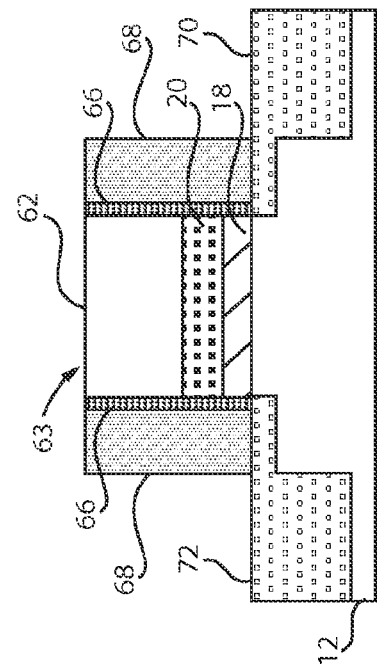
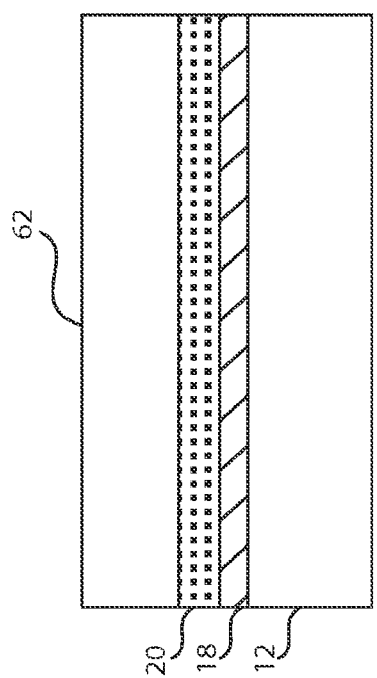
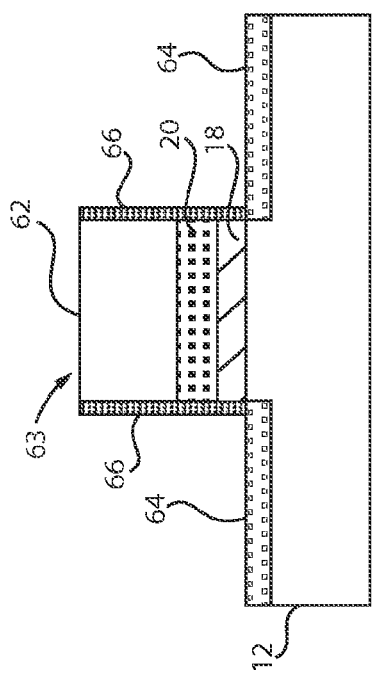

EXTENDED GATE SENSOR FOR PH SENSING

RELATED APPLICATION DATA

This application is a Continuation application of co-pending U.S. patent application Ser. No. 13/918,272 filed on Jun. 14, 2013, incorporated herein by reference in its entirety.

BACKGROUND

1. Technical Field

The present invention relates to integrated circuits, and more particularly to field effect transistor based sensing devices having an extended gate structure.

2. Description of the Related Art

The measurement of pH is important in many chemical and bio-chemical reactions. Sensors that measure pH may have multiple applications and in particular may provide measurements in processes, such as, DNA sequencing, enzymatic reactions where protons are produced, e.g., glucose detection, etc.

In many instances, pH sensors are included in integrated circuits. A floating gate field effect transistor (FET) pH sensor may be employed for sequencing DNA. A bead is coated with multiple copies of single DNA strands; nucleotides are flowed into a space or a well above a floating gate. The well includes dielectric walls and a metal oxide dielectric sensing layer. When a polymerization reaction occurs, protons are released into the well thus causing transient pH to change in the well. The pH change is sensed by the floating gate of the sensor, which is below the metal oxide sensing dielectric layer. The metal oxide dielectric layer is used as the pH sensing surface in contact with the solution.

Since the pH sensing surface is dielectric, only the bottom of the well is employed as the sensing surface. The sensing surface is limited by layout area restrictions, and the floating gate design and the pH (i.e., proton concentration) signal is limited based on the available sensing capabilities. As a result the pH sensitivity decreases.

SUMMARY

A sensing device includes a substrate having a source region and a drain region formed therein. A gate structure is formed over the substrate and includes a gate dielectric and a gate conductor. The gate conductor is formed on the gate dielectric and disposed between the source region and the drain region. A dielectric layer is formed over the substrate and has a depth configured to form a well over the gate conductor. A gate extension is formed in contact with or as part of the gate conductor and including a conductive material covering one or more surfaces of the well.

Another sensing device includes a substrate having a source region and a drain region formed therein, and a gate dielectric formed over the substrate. A dielectric layer is formed over the substrate and has a depth configured to form a well over a region between the source region and the drain region. A gate extension is formed in contact with the gate conductor and extends laterally outward parallel to a major surface of the substrate. The gate extension includes a conductive material exposed on at least one surface of the well and forming a gate conductor of the sensing device.

A method for forming a pH sensing device includes forming a gate structure over a substrate including a gate dielectric, a gate conductor and a dummy material, the gate conductor being formed on the gate dielectric and disposed between the source region and the drain region; forming a dielectric layer over the substrate and the gate structure; planarizing the dielectric layer to expose the dummy material; removing the dummy material to form a well; and forming a gate extension in contact with the gate conductor and including a conductive material covering one or more surfaces of the well.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a cross-sectional view of a sensing device having a plate structure at a bottom of a well in accordance with one embodiment;

FIG. 2 is a cross-sectional view of a sensing device having a u-shaped structure with angled side portions in a well in accordance with another embodiment;

FIG. 3 is a cross-sectional view of a sensing device having a u-shaped structure with angled side portions extending up a portion of a well depth in accordance with another embodiment;

FIG. 5 is a cross-sectional view of a substrate having a gate dielectric, a gate conductor and a dummy layer in accordance with one embodiment;

FIG. 6 is a cross-sectional view of the device in FIG. 5 after patterning a gate structure and forming sidewall spacers in accordance with the present principles;

FIG. 7 is a cross-sectional view of the device in FIG. 6 after an extension implant is performed adjacent to the gate structure in accordance with the present principles;

FIG. 8 is a cross-sectional view of the device in FIG. 7 after a second spacer is formed on sides of the gate structure and after a source and drain region implant and anneal in accordance with the present principles;

DETAILED DESCRIPTION OF PREFERRED EMBODIMENTS

Figure 4:
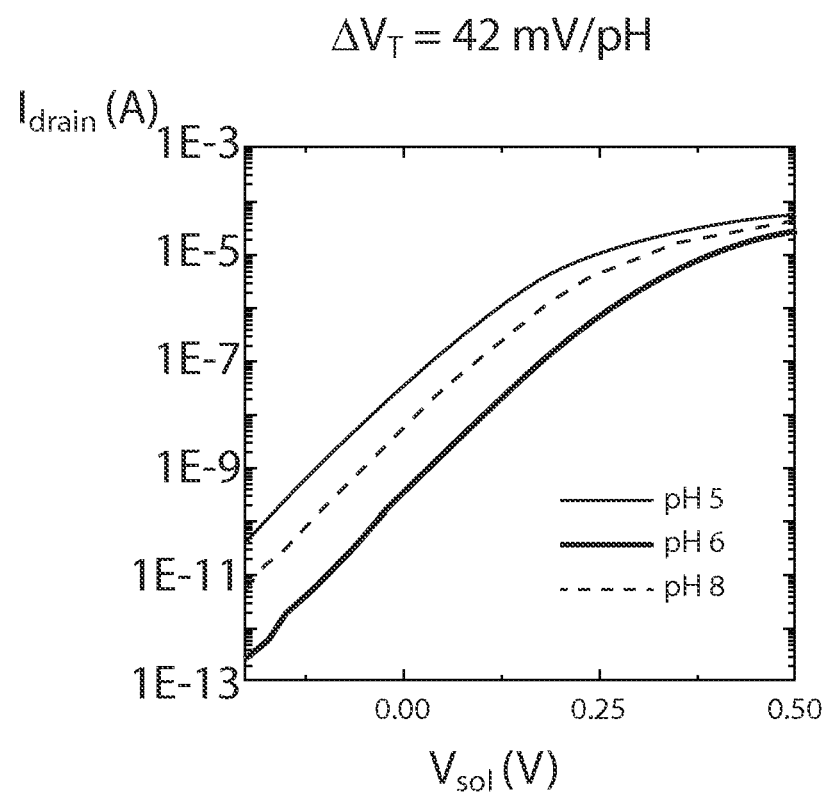
FIG. 4 is a plot of drain current (A) versus solution voltage (V) for different measured pH of a solution and showing a difference in threshold voltage for a field effect transistor sensing device in accordance with the present principles.

In accordance with the present principles, pH sensing devices and methods for fabrication are provided. In one embodiment, an extended gate field effect transistor (FET) sensor is provided where the extended gate forms a pH sensing surface. Since the gate includes a conductive material (e.g., an equi-potential surface), the well's entire surface can be employed as the pH sensing surface. This significantly increases pH sensing surface area and therefore increases pH sensitivity during DNA sequencing reactions or other applications.

In addition, the sensor structure in accordance with the present principles includes a simpler structure (e.g., no floating gate, dielectric metal oxide sensing surface). The sensor has a metal gate that forms the pH sensing surface. In one embodiment, the material for the metal gate may include TiN which is conducting (~10 of mico-ohm-cm) and pH sensitive, although other materials may be employed. The extended gate sensor may also include a cup or channel surface that increases contact area for pH sensing.

The present principles provide enhanced sensitivity due to an increase in sensing area and the device structure. A simpler sensor structure is provided with the metal gate also forming the pH sensing surface. Unlike the prior art, the present sensor structure does not have a floating gate and a metal oxide dielectric sensing surface. No issues arise with respect to alignment of a floating gate with a dielectric sensing layer.

It is to be understood that the present invention will be described in terms of a given illustrative architecture on a wafer or substrate; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a cross-sectional view of one embodiment of a sensing transistor 10 is illustratively shown. The transistor 10 may include a field effect transistor (FET) integrated on a substrate or wafer 12. Substrate 12 may include a monocrystalline silicon substrate, although other materials may be employed, e.g., germanium, silicon germanium, gallium arsenide, etc. Diffusion regions 14 and 16 are provided in the substrate 12 and include a source region (14) and a drain region (16). The source and drain regions 14, 16 have a conductive channel 15 therebetween, which conducts upon activation of a gate conductor 20. The gate conductor 20 is separated from the channel region 15 by a gate dielectric layer 18. It should be understood that the materials and structures for forming the diffusion regions 14, 16, the gate dielectric 18, the gate conductor 20, the dielectric layer 24, etc. may employ known processes and employ known materials.

The diffusion regions 14, 16 may include doped portions of the substrate 12. The gate dielectric layer 18 may include, e.g., a silicon oxide or a silicon nitride. The gate conductor 20 includes a conductive material, such as, e.g., TiN, TaN, Pt or similar conductive materials. It should be noted that the gate conductor 20 includes an extension portion 22 that expands a lateral distance of the gate conductor 20. The extension portion 22 preferably includes a same material as the gate conductor 20 and may be deposited during a same deposition process. For example, the gate conductor 20 and the gate extension portion 22 may be formed using a dual damascene process in a dielectric layer 24. In other embodiments, the gate conductor 20 and the gate extension portion 22 may be formed in separate processes and may include different materials A dielectric layer 26 is formed over the extension portions 22 and over the dielectric layer 24. The dielectric layer 26 is then patterned using a patterning process (e.g., photolithography, etc.) to open up a well 28 over the gate extension portion 22. The gate extension portion 22 forms a sensing layer that will be a pH sensitive metal film, which also forms the gate of the field effect transistor. The gate extension portion 22 extends through and forms a base of the well 28. It should be understood that while the present embodiments are illustratively directed to pH sensing, the present principles may be adapted to other applications such as sensing positive ions, electrons, negative ions, etc.

Referring to FIG. 2, a cross-sectional view of another embodiment of a sensing transistor 30 is illustratively shown. The transistor 30 may include a field effect transistor (FET) integrated on the substrate or wafer 12. It should be understood that the materials and structures for forming the diffusion regions 14, 16, the gate dielectric 18, the gate conductor 20, the dielectric layer 24, etc. may employ known processes and employ known materials.

The gate conductor 20 includes a conductive material, such as TiN, TaN, Pt or similar conductive materials. It should be noted that the gate conductor 20 includes an extension portion 32 that expands the gate conductor 20. The extension portion 32 includes a u-shaped portion having a lateral or base portion 33 and side portions 35. The extension portion 32 preferably includes a same material as the gate conductor 20 and may be deposited during a same deposition process. For example, the gate conductor 20 and the gate extension portion 32 may be formed using a dual damascene-like process in or on the dielectric layer 24. In other embodiments, the gate conductor 20 and the gate extension portion 32 may be formed in separate processes and may include different materials. For example, the gate conductor 20 may be formed in a first process, and the extension portion 32 may be formed by a conformal deposition over a patterned dielectric layer 36, which is formed over the gate conductor 20 and the dielectric layer 24 and is patterned to form a well 34.

The gate extension portion 32 forms a sensing layer that will be a pH sensitive metal film, which also forms the gate of the field effect transistor. The gate extension portion 32 extends through and forms a base and sides of the well 34 providing a large sensing area and therefore higher pH sensitivity. It should be understood that while the gate extension portion 32 is depicted with a u-shape, other shapes and configurations are contemplated, for example, the gate extension portion 32 may include the lateral portion 33 and one side portion 35, the gate extension portion 32 may form a cup or cup-like shape, a v-shape, etc. To further extend the surface area, the vertically disposed portions 35 may be set on an angle relative to portion 33. For example the angle, $\alpha$, may be greater than 90 degrees for each portion 35.

Referring to FIG. 3, a cross-sectional view of another embodiment of a sensing transistor 50 is illustratively shown. The transistor 50 may include a field effect transistor (FET) integrated on the substrate or wafer 12. It should be understood that the materials and structures for forming the diffusion regions 14, 16, the gate dielectric 18, the gate conductor 20, the dielectric layer 24, etc. may employ known processes and employ known materials.

The gate conductor 20 includes a conductive material, such as TiN, TaN, Pt or similar conductive materials. It should be noted that the gate conductor 20 includes an extension portion 42 that expands the gate conductor 20. The extension portion 42 includes a u-shaped portion having a lateral or base portion 43 and side portions 45. The extension portion 42 preferably includes a same material as the gate conductor 20 and may be deposited during a same deposition process. For example, the gate conductor 20 and the gate extension portion 42 may be formed using a dual damascene-like process in or on the dielectric layer 24. In other embodiments, the gate conductor 20 and the gate extension portion 42 may be formed in separate processes and may include different materials. For example, the gate conductor 20 may be formed in a first process, and the extension portion 42 may be formed by a conformal deposition over a patterned dielectric layer 46, which is formed over the gate conductor 20 and the dielectric layer 24 and is patterned to form a well 44 (or portion of a well).

The gate extension portion 42 forms a sensing layer that will be a pH sensitive metal film, which also forms the gate of the field effect transistor. In this embodiment, the gate extension portion 42 includes smaller side portions 45 than those of the embodiment shown in FIG. 2. This structure 50 may be provided if errors occur due to the flow of protons from one well 44 to a neighboring well. These errors could occur when wells are packed too close together. In FIG. 3, after forming the gate extension portion 42 (e.g., by blanket deposition over a dielectric layer 46) and a chemical mechanical polish (CMP). An additional dielectric layer 48 is deposited and patterned to open up well 44.

The gate extension portion 42 extends through and forms a base and sides (partially) of the well 44 providing a large sensing area and therefore higher pH sensitivity. It should be understood that while the gate extension portion 42 is depicted with a u-shape, other shapes and configurations are contemplated, for example, the gate extension portion 42 may include the lateral portion 43 and one side portion 45, the gate extension portion 42 may form a cup or cup-like shape, a v-shape, etc.

Referring to FIG. 4, a plot of sensing current ($I_{drain}$ (A)) is plotted against solution voltage ($V_{sol}$ (V)) for an FET with an extended TiN gate (FIG. 2), which also forms the pH sensing surface. The TiN gate potential depends on the proton concentration (pH) in the solution. As the pH changes, the gate potential changes, which causes the sensing drain current to change exponentially provided the voltage applied to the solution is in the sub-threshold regime. From FIG. 4, we can observe that as pH changes, the sensing current ($I_{drain}$) versus $V_{sol}$ curves shift by about 42 mV/pH, thus providing a measure of pH.

The present structures employ metal as the pH sensing surface. Since metals are conducting and therefore provide an equi-potential surface, the sensing surface can be increased to form bottoms and walls of the well. This increases sensing surface results in higher pH sensing. The metals that can be used for pH sensing include TiN, TaN, Pt, etc.

The present structures employ FETs with the metal gate as the pH sensing surface. This is a simpler structure and does not pose alignment issues between a floating gate and a well bottom as in conventional sensors. In particularly useful embodiments, the extended gate FET sensor may be employed for DNA sequencing, glucose sensing (e.g., beads coated with glucose oxidase would be loaded; pH would change upon glucose addition), biochemical reactions that result in proton production/consumption, acetylcholine detection (in presence of acetylcholone esterase), urea detection (in presence of urease), penicillin detection (in presence of penicillanse), etc.

FIGS. 5-12 show an illustrative fabrication sequence for building a sensor in accordance with the present principles.

Referring to FIG. 5, a cross-sectional view shows a substrate 12 having a gate dielectric layer 18, a gate conductor 20 and a dummy layer 62 formed thereon. The substrate 12 may include a monocrystalline silicon substrate having doped wells formed therein for device formation. The gate dielectric layer 18 may include an oxide, such as silicon oxide or a high-k dielectric. The gate conductor 20 may include a layer of TiN. TaN, Pt or other suitable conductive material. The dummy layer 62 may include a selectively removable material, such as polysilicon.

Referring to FIG. 6, the layers 18, 20 and 62 are patterned to form a gate structure 63. The gate structure 63 has a spacer 66 formed on sidewalls thereof by employing a deposition process, e.g., SiN, and etching.

Referring to FIG. 7, an extension dopant region 64 is formed by performing an implantation or diffusion process to drive in dopants on sides of the gate structure 63 and below the sidewalls spacers 66.

Referring to FIG. 8, second spacers 68 are formed on sidewall spacers 66. The second spacers 68 may include a silicon oxide material. The second spacers 68 may be formed using a conformal deposition followed by an etching process. The second spacers 68 are followed by formation of source and drain regions 70, 72. These regions 70, 72 may be formed by an implantation process and then annealed to activate the diffusion regions 70, 72.

Figure 9:
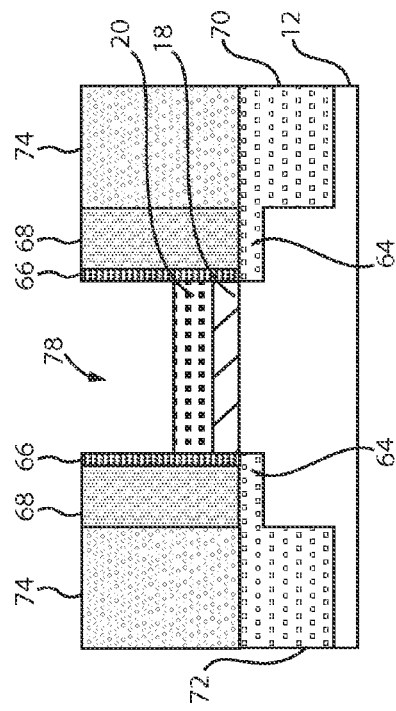
FIG. 9 is a cross-sectional view of the device in FIG. 8 after an interlevel dielectric layer is formed and planarized in accordance with the present principles.

Referring to FIG. 9, an interlevel dielectric layer 74 is formed over the device. The interlevel dielectric layer 74 is planarized to provide a planarized surface 76. The planarization process may be performed by a CMP process.

Figure 10:
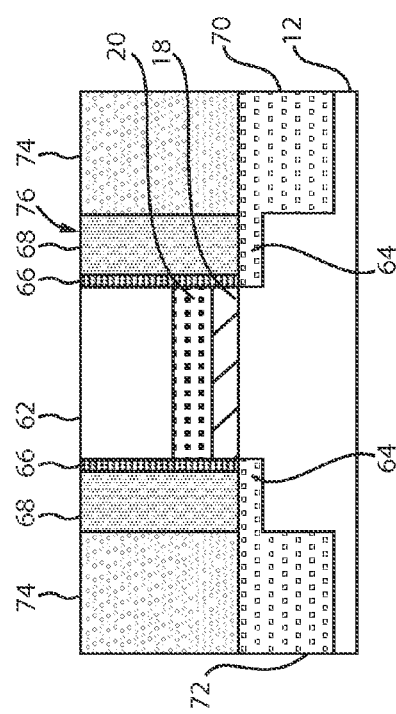
FIG. 10 is a cross-sectional view of the device in FIG. 9 after the dummy layer is selectively etched from the gate structure to form a well in accordance with the present principles.

Referring to FIG. 10, the dummy layer 62 is removed to form a well 78. The dummy layer 62 may be removed using an etching process, which is selective to the spaces 66, 68 and the interlevel dielectric layer 74. It should be understood that the etching process may be adjusted to create angled sidewalls for the well 78.

Figure 11:
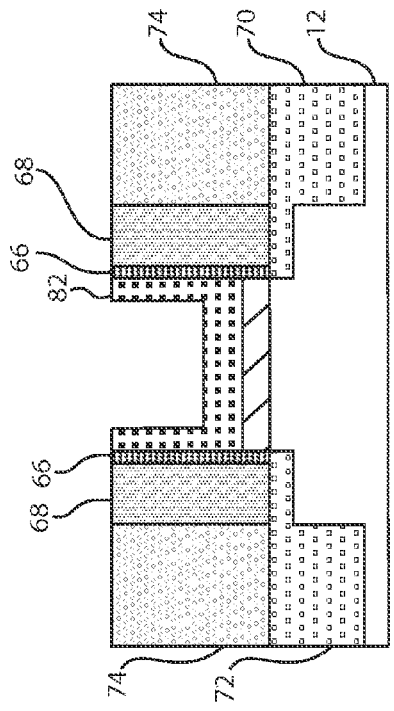
FIG. 11 is a cross-sectional view of the device in FIG. 10 showing a second conductive material formed in the well in accordance with the present principles.

Referring to FIG. 11, a second conductive material 80 is deposited. It should be noted that the second conductive material 80 may be deposited on top of the gate conductor 20 or the gate conductor 20 may be formed along with the second conductive material 80 (e.g., from the second conductive material 80). The second conductive material 80 can be deposited over the gate conductor 20 (or the gate dielectric 18), spacer 66, spacers 68 and the interlevel dielectric layer 74.

Figure 12:
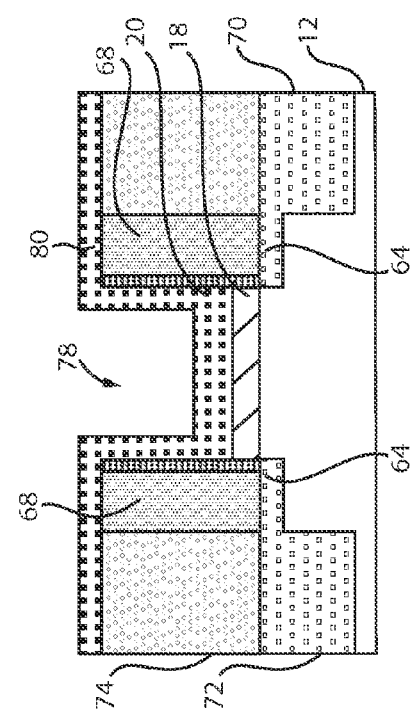
FIG. 12 is a cross-sectional view of the device in FIG. 11 showing the second conductive material formed into a gate extension in accordance with the present principles.

Referring to FIG. 12, a spacer etch, or planarization process may be performed to complete a gate extension 82. The gate extension 82 may include other geometric configurations, such as, e.g., sloped side portions, only one side portion, multiple walls between side portions (e.g., vertical walls extending from a middle portion of the horizontal base of the gate extension 82), etc. It should be understood that other structures and features may be included, such as metal lines, contacts, other electronic components, etc.

Figure 13:
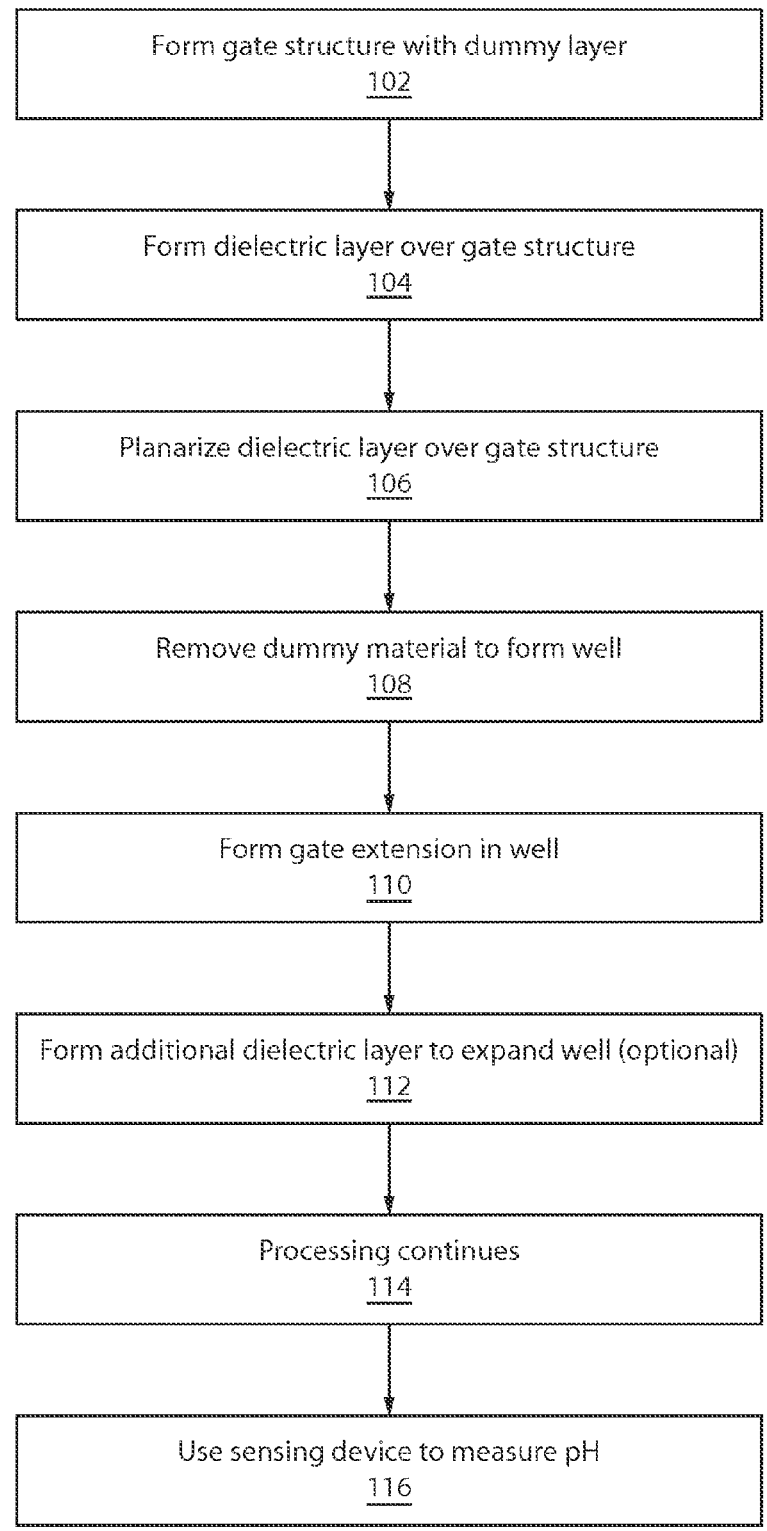
FIG. 13 is a block/flow diagram showing a method for fabricating a pH sensing device in accordance with illustrative embodiments.

Referring to FIG. 13, a method for forming a pH sensing device is shown in accordance with illustrative embodiments. It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In block 102, a gate structure is formed over a substrate including a gate dielectric, a gate conductor and a dummy material, the gate conductor being formed on the gate dielectric. A source region and a drain region are formed adjacent to the gate structure. The source and drain regions are formed in the substrate adjacent to the gate structure and preferably include extension diffusion regions. The gate structure may include one or more sets of sidewall spacers to protect the gate structure during and after processing. In block 104, a dielectric layer is formed over the substrate and the gate structure. In block 106, the dielectric layer (e.g., interlevel dielectric) is planarized to expose the dummy material. In block 108, the dummy material is removed to form a well. This may include a selective etch process.

In block 110, a gate extension is formed in contact with the gate conductor and includes a conductive material covering one or more surfaces of the well. Forming the gate extension may include forming one or more of a plate, a cup-like structure, a u-shaped structure, etc. on one or more surfaces of the well. The conductive material may include one of TiN, TaN and Pt. In one embodiment, the gate extension and the gate conductor may be concurrently formed and/or include a same material.

In block 112, an additional dielectric layer may be formed over the gate structure and etched to increase the size of the well. This may be employed in the case of the device in FIG. 3, for example. In block 114, processing continues to complete the device, e.g., form connections and other structures. In block 116, the sensing device is employed to measure pH or other property for a fluid in the well.

Having described preferred embodiments for an extended gate sensor for pH sensing (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for forming a pH sensing device, comprising:
    forming a gate structure over a substrate including a gate dielectric, a gate conductor and a dummy material, the gate conductor being formed on the gate dielectric and disposed between a source region and a drain region;
    forming a dielectric layer over the substrate and the gate structure, wherein the dielectric layer is disposed at least laterally spaced from the dummy material;
    planarizing the dielectric layer to expose the dummy material;
    removing the dummy material to form a well; and
    forming a gate extension in contact with the gate conductor and including a conductive material covering one or more surfaces of the well.

2. The method as recited in claim 1, wherein forming the gate extension includes forming one of a plate, a cup-like structure and a u-shaped structure on one or more surface of the well.

3. The method as recited in claim 1, further comprising measuring pH of a fluid in the well.

4. The method as recited in claim 1, wherein the conductive material includes one of TiN, TaN and Pt.

5. The method as recited in claim 1, further comprising forming first spacers extending from the substrate to a top surface of the dummy material.

6. The method as recited in claim 5, wherein the first spacers protect the gate structure from subsequent processes.

7. The method as recited in claim 5, further comprising forming second spacers adjacent to the first spacers.

8. The method as recited in claim 1, wherein removing the dummy material includes forming sloped sidewalls of the well.

9. The method as recited in claim 8, wherein forming the gate extension includes at least one vertical portion being disposed on an angle relative to a base portion of the gate extension.

10. The method as recited in claim 9, wherein the at least one vertical portion covers less than an entirety of the sidewalls.

11. The method as recited in claim 1, wherein forming the gate extension includes forming at least one vertical wall extending from a middle portion of a horizontal base of the gate extension.

12. The method as recited in claim 1, wherein the dielectric layer is laterally spaced from the gate extension by one or more intervening elements.

13. The method as recited in claim 1, wherein forming the gate extension and the gate conductor include forming the gate extension and the gate conductor from a same material.

* * * * *